United States Patent
Gobius Du Sart et al.

(10) Patent No.: US 10,627,347 B2
(45) Date of Patent: Apr. 21, 2020

(54) QUANTIFICATION METHOD OF IMPURITIES IN LACTIDE

(71) Applicant: PURAC BIOCHEM BV, Gorinchem (NL)

(72) Inventors: Gerrit Gobius Du Sart, Gorinchem (NL); Jan Arie Niessen, Gorinchem (NL); Vincent De Jong, Gorinchem (NL)

(73) Assignee: PURAC BIOCHEM BV, Gorinchem (NL)

( * ) Notice: Subject to any disclaimer, the term of this patent is extended or adjusted under 35 U.S.C. 154(b) by 0 days.

(21) Appl. No.: 15/038,583

(22) PCT Filed: Dec. 8, 2014

(86) PCT No.: PCT/EP2014/076830
§ 371 (c)(1),
(2) Date: May 23, 2016

(87) PCT Pub. No.: WO2015/086494
PCT Pub. Date: Jun. 18, 2015

(65) Prior Publication Data
US 2016/0299071 A1    Oct. 13, 2016

(30) Foreign Application Priority Data
Dec. 10, 2013    (EP) .................................... 13196357

(51) Int. Cl.
*G01N 21/3577*    (2014.01)
*G01N 21/59*    (2006.01)
(Continued)

(52) U.S. Cl.
CPC ........... *G01N 21/59* (2013.01); *C07D 319/12* (2013.01); *G01N 21/359* (2013.01); *G01N 2201/0826* (2013.01); *G01N 2201/12* (2013.01)

(58) Field of Classification Search
CPC ........... G01N 21/6428; G01N 21/6458; G01N 21/6408; G01N 21/645; G01N 21/6452
See application file for complete search history.

(56) References Cited

U.S. PATENT DOCUMENTS

| | | | |
|---|---|---|---|
| 5,023,350 A | 6/1991 | Bhatia | |
| 2005/0222379 A1* | 10/2005 | Matsuo | B01J 19/1862 528/359 |
| 2013/0267675 A1* | 10/2013 | Yoshida | B01D 1/22 528/361 |

FOREIGN PATENT DOCUMENTS

| | | |
|---|---|---|
| EP | 0 339 882 A1 | 11/1989 |
| JP | 2000-086652 A | 3/2000 |
| JP | 2011-173844 A | 9/2011 |

OTHER PUBLICATIONS

Inkinen et al. "From Lactic Acid to Poly(lactic acid)(PLA): Characterization and Analysis of PLA and its Precursors", Biomacromolecules 2011, p. 523-532.*

(Continued)

*Primary Examiner* — David P Porta
*Assistant Examiner* — Mamadou Faye
(74) *Attorney, Agent, or Firm* — Oliff PLC

(57) ABSTRACT

A method for quantification of the amount of impurities in lactide. The method is characterized in that the quantification of the impurities is based on measurements performed on absorptions in the near Infra-Red region of the electromagnetic spectrum. With this method, small amounts of impurities like water, free-acid species or both can be determined online in a reaction mixture of lactide in a (Continued)

Figure 1:
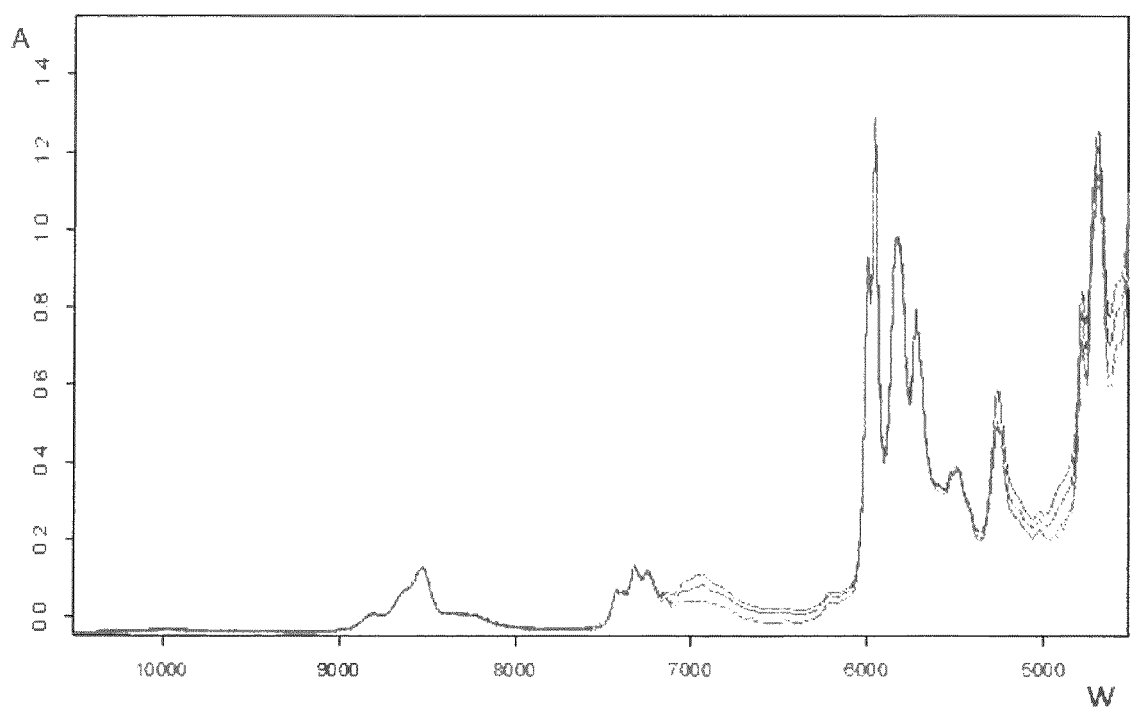

relatively simple manner. This allows a simple online monitoring of the production process of lactide.

10 Claims, 3 Drawing Sheets

(51) Int. Cl.
 *C07D 319/12* (2006.01)
 *G01N 21/359* (2014.01)

(56) References Cited

OTHER PUBLICATIONS

Andre "New Double-Responsive Micelles of Block Copolymers based on, NN-Diethylacrylamide: Synthesis, Kinetics, Micellization, and Application as Emulsion Stabilizers", Dissertation, Universite Pierrre et Marie Curie, Paris VI, Bayreuth, 2005, p. 1-233.*
Ozaki et al. "Near-Infrared Spectroscopy in Food Science and Technology", Wiley-Interscience, Sep. 7, 2006, p. 1-408.*
Ronnest "Analysis of Multivariate Sensor Data for Monitoring of Cultivations", DTU Chemical Engineering, Department of Chemical and Biochemical Engineering, PhD Thesis, Jul. 2010, p. 1-171. (Year: 2010).*
Cervera et al. "Application of Near-Infrared Spectroscopy for Monitoring and Control of Cell Culture and Fermentation", American Institute of Chemical Engineers, Sep. 28, 2009 Wiley InterScience p. 1561-1581 (Year: 2009).*

Jul. 17, 2017 Office Action issued in European Patent Application No. 14809007.9.
Keyworth, D.A., "Determination of Water by Near-Infrared Spectrophotometry," Wyandotte Chemicals Corp., 1961, pp. 461-469. vol. 8, Pergamon Press Ltd.
Meeker,"Water Determination by Near Infrared Spectrophotometry," Analytical Chemistry, Oct. 1962, vol. 34, No. 11, pp. 1510-1511.
Jan. 21, 2015 Search Report issued in International Patent Application No. PCT/EP2014/076830.
Jan. 21, 2015 Written Opinion issued in International Patent Application No. PCT/EP2014/076830.
Braun, Birgit et al., "Infrared Spectroscopic Determination of Lactide Concentration in Polylactide: An Improved Methodology", Macromolecules, Dec. 1, 2006, vol. 39, No. 26, pp. 9302-9310.
Feng, Lidong et al., "A quantitative HPLC method for determining lactide content using hydrolytic Kinetics", Polymer Testing, Sep. 1, 2009, vol. 28, No. 6, pp. 592-598.
Luypaert, J. et al., "Near-infrared spectroscopy applications in pharmaceutical analysis", Talanta, Apr. 27, 2007, vol. 72, No. 3, pp. 865-883.
Inkinen, Saara et al., "From Lactic Acid to Poly(lactic acid) (PLA): Characterization and Analysis of PLA and Its Precursors", Biomacromolecules; Mar. 14, 2011, vol. 12, No. 3, pp. 523-532.
Aug. 1, 2017 Office Action issued in Japanese Patent Application No. 2016-536854.
Mar. 5, 2018 Office Action issued in Chinese Patent Application No. 201480066095.5.
Nan et al., "Synthesis and purification of D,L-Lactide," Petrochemical Technology, vol. 32, No. 12, 2003, pp. 1073-1077.

* cited by examiner

QUANTIFICATION METHOD OF IMPURITIES IN LACTIDE

FIELD OF THE INVENTION

The present invention relates to a method for quantification of the amount of impurities in lactide.

BACKGROUND OF THE INVENTION

Lactide is a well-known intermediate product in the manufacturing of polymer materials, like polylactic acid (PLA) or PLA-containing copolymers. Lactide (sometimes called dilactide) is a cyclic dimer of lactic acid and is usually manufactured by means of a two-step process. In the first step, lactic acid is polymerized into a so-called pre-polymer or oligomer, having a relatively low molecular weight. In the second step, crude lactide is formed from this pre-polymer by means of a so-called 'backbiting' process in the presence of a catalyst. This crude lactide material may be purified by means of (repeated) crystallization and/or (repeated) distillation. The so-obtained purified lactide may subsequently be used in a polymerization process for the manufacture PLA or PLA-containing copolymers.

It is well-known that lactide can exist in three different geometric structures, which have a diastereomeric relationship. These different structures can be distinguished as R,R-lactide (or D-lactide), S,S-lactide (or L-lactide) and R,S-lactide (or meso-lactide). Mixtures of equal amounts of D- and L-lactide are often referred to as racemic lactide or rac-lactide. Within the scope of the present invention, the word 'lactide' refers both to the three pure lactides (being composed of only one diastereomer) as well as to mixtures of two or more of the pure lactides.

The purity of lactide is an important issue. This is especially true as impurities may have a strong influence on the polymerization of lactide into PLA. In view therefore, it is relevant to have available methods which allow the determination of the amounts of impurities in lactide. Such methods should have a high accuracy and reliability. Such methods should moreover be simple in their use and implementation in lactide handling processes.

Well-known impurities in lactides are species with hydroxyl groups and/or carboxylic acid groups. Water and free acid species are important examples of these types of impurities. In view thereof, the amount of such impurities in the lactide material should be kept as low as possible. Repeated distillation and repeated crystallization techniques of different types are well-known technical purification means which can be used during the production of lactide for lowering the amount of the mentioned impurities as much as possible.

Currently, titration methods are often used to determine the amount of impurities, like species with hydroxyl groups and/or carboxylic acid groups, in lactide. For executing these methods, small samples of lactide-containing material need to be taken and handled by different titration procedures in order to determine the exact amount of different impurities.

According to the experience of the inventors, the known titration methods for quantification of impurities in lactide are rather cumbersome and labor-intensive in their use. Moreover, the results of such quantification methods are not immediately available. Therefore, determination of the impurities by means of the known titration methods has the drawbacks of being relatively expensive and less suitable to monitor the lactide quality online under mass production circumstances.

SUMMARY OF THE INVENTION

In Applicants views, there exists a strong need to simplify the known quantification method of impurities in lactide material. It is therefore an object of the present invention to provide an accurate yet simple, flexible and cost-effective method for the quantification of impurities in lactide, which method does not require a time-consuming and complicated experimental handling. Such quantification method should preferably be operable in various stages of a lactide production process and should also be operable in the monitoring of the quality of lactide during its storage.

These and possible further objects of the present invention are achieved by means of a method for quantification of the amount of impurities in lactide, which method is further characterized in that the quantification of the impurities is based on measurements performed on absorptions in the near Infra-Red region of the electromagnetic spectrum.

The invention is based on the experimentally obtained insight of the inventors that rather small amounts of impurities can be measured and quantified in a lactide material by means of near Infra Red (nIR) measurements. By using this method, amounts of impurities as small as 0.1% by weight or less in lactide can be measured and quantified in an accurate and reproducible manner. Compared with the known titration methods, the invented method appears to be more accurate when performed under optimal conditions. Moreover, the handling for performing the nIR measurements, like the sample preparation and the data analysis, is far less time-consuming as compared to said commonly used titration methods. In practice, determining impurity levels by means of titration takes at least several hours after taking the sample to be measured. This means that these titration methods are not suited for process control purposes.

It is noted that in practice the nIR spectrum is defined to range from approximately 12000-4000 $cm^{-1}$. In this spectral range, molecular overtone and combination vibrations of lactide and the impurities present in the lactide appear to be visible. The corresponding absorption peaks are rather broad and overlapping, resulting in complex nIR spectra. In these spectra, the various peaks cannot unambiguously be assigned to specific vibrations. Nevertheless, nIR measurements on samples containing mixtures of well-determined amounts of both one and two specific impurities and lactide surprisingly show that calibration curves with very good fits can be obtained. It can therefore be concluded that very small amounts of such impurities in lactide can be quantified in a simple manner by means of nIR.

A preferred embodiment of the method according to the present invention is characterized in that the impurities comprise water. Even small traces of moisture or water in lactide are known to have negative effect on the properties and shelf life of such lactide. There is a general trend to keep the amount of water in lactide below a threshold value of 100 ppm, more particularly below a tress hold value of 50 ppm. Threshold values of 20 ppm or less can be accurately and reproducibly measured with the method according to the present invention. Said method is therefore very suitable for use in monitoring the (change of) the amount of moisture in lactide samples under various conditions, both online during its production and off-line during its storage.

Another preferred embodiment of the invented method is characterized in that the impurities comprise free acid species. The phrase 'free acid species' stands for any acidic species which can be expected in lactide, including lactic acid, lactoyl lactic acid and lactic acid oligomers as well as oxidative degradation products like 2-pyruvoyloxypropanoic acid. These impurities in lactide contain at least one free carboxylic acid group. At least part of these impurities can be formed by means of degradation of lactide. The amounts of these degradation products should be kept as small as possible, preferably below 10 mmol per kg lactide. Threshold values of 5 mmol/kg or even less can be accurately and reproducibly measured with the method according to the present invention. Said method is therefore very suitable for use in monitoring the (change of) the amount of free acid in lactide samples under various conditions.

Also preferred is the embodiment of the invented method which is characterized in that the amount of impurities is measured in lactide being in a liquid aggregate phase. The inventors have found that the invented quantification method is easily realized at temperatures at which the lactide is in liquid form. In practice this means that the measurements should be performed at temperatures above approximately 55° C. for measuring impurities in meso-lactide and above approximately 100° C. for measuring impurities in L- or D-lactide as well as mixtures of latter two lactides.

Interesting is also the embodiment of the method according to the present invention which is characterized in that the amount of impurities is measured in lactide being in a solid aggregate phase. In practice this implies that the amount of the mentioned impurities in any type of lactide can satisfactorily be measured at ambient temperature (or any other temperature lower than the melting point of said lactide). The solid lactide may be present various forms, like as a powder, as grains, as flakes or as pellets. Therefore, the invented method allows for quality control of solid lactide, irrespective of its type (R,R-, S,S- or R,S and even mixtures of these three types) over a long period of time, said lactide being stored and/or transported during this period of time.

Much interest is also given to the embodiment of the present invention, which is characterized in that in the amount of impurities is measured in a lactide production process in which lactide is prepared by depolymerization of oligomers of lactic acid. The lactide obtained by this process is liquefied from the vaporous aggregate state, shortly after its production. As from this stage in the production process, inline nIR measurements can be performed on the liquefied lactide in order to monitor its quality. Said liquefied lactide may afterwards be solidified by means of one or more crystallization steps, if needed after one or more distillation steps. The lactide quality may be monitored during the whole purification process.

Also of interest is the embodiment of the invented method which is characterized in that in that the production process is a batch process. In this preferred embodiment of the method according to the current invention, the quantification of the amount of impurities can be performed at any desired stage of the lactide production process. It is even possible to monitor in time the whole reaction, i.e. to continuously quantify the change in the concentration of free acid and water in the reaction mixture from the start of the lactide production until its completion.

Interesting is also the embodiment of the method of the invention which is characterized in that the lactide production process is a continuous process. In such continuous process, the amount of impurities like water and free acid can be quantified on certain points of interest in the lactide production equipment. In case of more points of interest, like in the crude liquid lactide and in (partly) purified liquid lactide, said quantification of impurities can be performed by using multiple measuring probes in combination with a single nIR measuring apparatus. The resulting data can be calculated instantaneously and preferably with a single data calculator. So, online monitoring of the change in the measured impurities in a continuous lactide production process is now possible. As a result of the present invention, the process and quality control of such a continuous process has become much simpler. Moreover, undesired deviations in the water and/or free acid species content occurring during the lactide production process can be determined at a very early stage, so that changes in process parameters to repair these deviations can be applied in an early stage. As a result, possible product loss can be minimized.

The invented quantification method can be performed with any state of the art near Infra Red measurement apparatus. Although measurements in the nIR spectral range between 6100 and 5100 cm$^{-1}$ provide most relevant information (first overtones), measurements in a broader nIR range like between 12000 and 4000 cm$^{-1}$ provide more accurate data, as this broader range may include second and higher overtones of the impurities to be measured as well as the lactide in which these impurities are present. Such nIR apparatus may comprise a measuring chamber, which chamber is provided with a near Infra Red source and a measuring probe. Latter probe may be connected via an optical fiber to the near Infra Red source as well as a software module. An apparatus of this design is especially suitable for online measuring of impurities in lactide production processes. Especially preferred is a nIR apparatus which is equipped with a number of probes which are all connected to the nIR source via optical fibers. Such apparatus having two or more probes is very suitable for use in a continuous lactide production process in which impurity concentrations in should be simultaneously monitored at different stages of said process, like just before and after a lactide purification step.

Compared with the apparatus needed for mid Infra-Red measurements, there is a significant advantage in terms of signal transportation from measurement probe to measurement device. In this respect, it is noted that the range of mid Infra Red signal transport via state of the art optical fibers is rather limited (few meters) due to signal losses. However, near Infra Red signals can be transmitted for tens of meters through the same optical fibers without significant losses. So, in principle a single nIR apparatus with several probes connected via optical fibers can be used for monitoring a complete lactide manufacture in a lactide production plant.

BRIEF DESCRIPTION OF THE INVENTION

Figure 2:
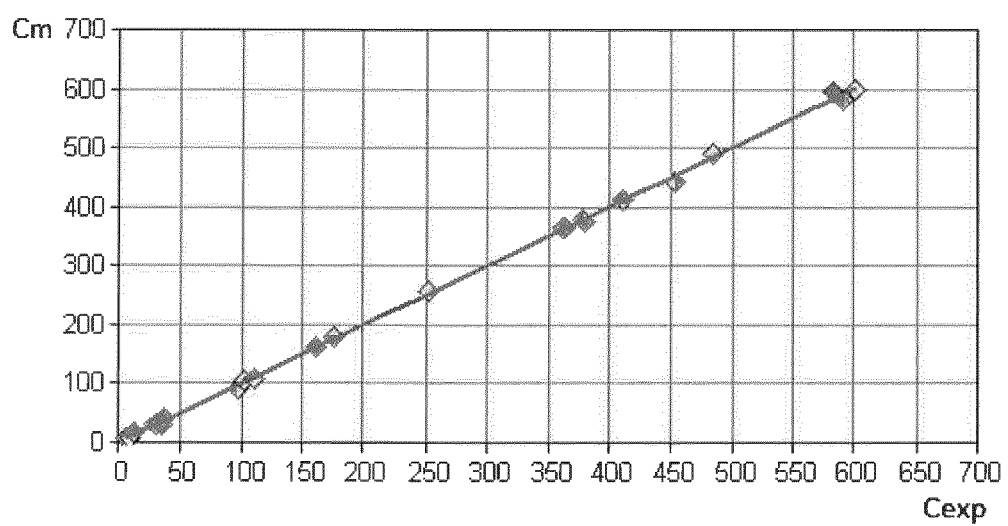
Figure 3:
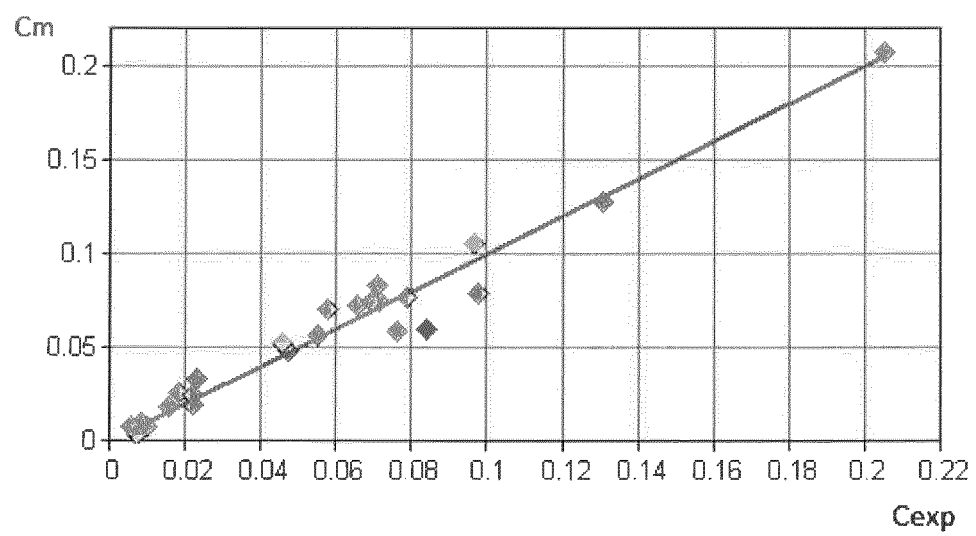

The present invention is described in more detail and elucidated by different examples and a drawing, in which FIG. 1 shows an overlay of several nIR spectra of lactide with different amounts of free acid species and water, FIG. 2 shows a cross validation plot of measured and calculated data of free acid species concentrations in lactide, and FIG. 3 shows a cross validation plot of measured and calculated data of water concentrations in lactide.

DETAILED DESCRIPTION OF THE INVENTION

In an experiment, approximately 550 grams of lactide (freshly prepared with an extreme low amount of free acid species and water) was melted under a nitrogen blanket in a round bottom flask of 500 ml with 4 necks by a heating jacket. The temperature of the lactide inside the round bottom flask was controlled by a special temperature controller. A nIR probe was inserted in the lactide liquid aggregate phase and the data acquisition was started. Every 17 seconds a spectrum was acquired. The amounts of the impurities were determined by titration, more particularly with a Karl Fischer titration method for the water content and a titration with Potassium Methanoate to determine the amount of free acid species. The titration was performed using a Titrino 736 apparatus with a 730 autosampler. The moment of sampling was used to connect the results with a single nIR spectrum which was used to develop a corresponding measuring model.

In FIG. 1 an overlay of several nIR spectra is shown, in which the absorption A is depicted as a function of the wave number W (in cm$^{-1}$). In more detail, this Figure shows a series of nIR spectra of the measured lactide in liquid state in which determined amounts of water and free acid species are present. The spectra of the lactide in liquid aggregate state were recorded in transmission mode over the range between approximately 12000 and 4000 cm$^{-1}$. The water content and free acid species content of the lactide samples of which the spectra are shown ranged between 10-381 mmol per kg lactide and 0.0113-0.695% (w/w), respectively. The measurements were performed with a Bruker MPA Matrix F duplex NIR spectrometer. Peaks of particular interest for the quantification method according to the present invention are located in the spectral range between 7300 and 4500 cm$^{-1}$. This is the area in which vibrations of the molecular OH-bonds in the different molecules of interest show overtones.

FIG. 2 shows a so-called cross-validation curve of measured amounts of free acid (in mmol/kg) in the freshly prepared lactide. In this Figure, the modeled concentration ($C_m$) is plotted as a function of the experimentally determined concentration ($C_{exp}$). In order to determine these curves, small amounts of lactic acid were added to the mixture during a period of time. At a number of time slots, a measuring sample was taken from the flask, which sample was frozen and the amount of free acid was determined by titration. At the moment of sample taking, a nIR spectrum was recorded over the indicated area. Based on the titration results, the recorded spectra and the software used, the plotted best-fit curves could be obtained for both the calibration curve and the cross validation curve.

From FIG. 2, it can be concluded that with the used nIR method it is possible to determine the amount of free acid species in pure lactide within a range of 6 to 600 mmol/kg with a confidence interval of 4 mmol/kg (SECV, this is the error for the whole model, at the lower part of the calibration line this error becomes 1 mmol/kg). In these early experiments, it was not possible to test the system at lower free acid numbers because the material had to be melted and small amounts of air can enter the set-up resulting in adsorption of water which is then (partly) converted to free acid. In later experiments, it was confirmed that free acid species amounts as low as 2 mmol/kg lactide could be measured with nIR with a confidence level RMSECV of 0.33 mmol/kg (cross validation plot not shown).

FIG. 3 shows a cross-validation curve of measured amounts of water (in %.w/w) in the freshly prepared lactide. In this Figure, the modeled concentration ($C_m$) is plotted as a function of the experimentally determined concentration ($C_{exp}$). In order to determine these curves, the above-mentioned sample was allowed to absorb water during a period of time. At a number of time slots, a measuring sample was taken from the flask, which sample was frozen and the amount of water was determined by titration. As the moment of sample taking, a nIR spectrum was recorded over the indicated area. Based on the titration results, the recorded spectra and the software used, the plotted best-fit curves could be obtained for both the calibration curve and the cross validation curve.

From FIG. 3, it can be concluded that with the used nIR method it is possible to determine the amount of water in pure lactide within a range of 0.006 to 0.2% (w/w) with a confidence interval of 0.01% (w/w). The accuracy of the determination of water is less good compared with the accuracy of the amount of free acid species (correlation coefficient 0.9681 versus 0.9999). This is partly due to the fact that the used reference method has a larger confidence interval.

The Relative Standard Deviation (RSD) of the free acid titration is less than 2.5%. For the water titration the RSD is much higher. The samples are very sensitive to moisture from the air. The lower precision of the water determination is most likely caused by the stability of the sample and the time it takes between sampling and analysing (a few minutes). The precision of the NIR method will be equal or less compared to the precision of the used reference method.

In addition to the above mentioned experimental results, it has also been shown that both mentioned impurities (water and free acid) can be measured and quantified simultaneously in lactide samples.

In summary, it has been shown that, with the presently invented lactide quantification method, small amounts of impurities like water and free-acid can be determined online in a reaction mixture of lactide in a relatively simple manner. This allows a simple online monitoring of the production process of lactide.

While the invention has been illustrated and described in detail in the foregoing description, such description is to be considered illustrative or exemplary and not restrictive; the invention is not limited to the disclosed embodiments and experiments. Variations to the disclosed embodiments can be understood and effected by those skilled in the art in practicing the claimed invention, from a study of the disclosure and the appended claims.

In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage.

The invention claimed is:

1. Method for quantification of impurities in lactide, comprising obtaining absorption spectra of the lactide in a near Infra-Red region of the electromagnetic spectrum ranging from 12000 cm$^{-1}$ to 4000 cm$^{-1}$ so as to capture second and higher overtones of the lactide and of the impurities, and quantifying an amount of the impurities in the lactide by performing measurements on the obtained absorption spectra, wherein the lactide is a cyclic dimer of lactic acid, and wherein the impurities are impurities bearing hydroxyl and/or carboxylic acid groups.

2. Method according to claim 1, wherein the impurities comprise water.

3. Method according to claim 1, wherein the impurities comprise free acid species.

4. Method according to claim 1, wherein the amount of impurities is quantified in lactide being in a liquid aggregate phase.

5. Method according to claim 1, wherein the amount of impurities is quantified in lactide being in a solid aggregate phase.

6. Method according to claim 1, wherein the amount of impurities is quantified during a lactide production process based on the measurements performed on the absorption spectra that are obtained in lactide prepared by depolymerization of oligomers of lactic acid.

7. Method according to claim 6, wherein the lactide production process is a batch process.

8. Method according to claim 6, wherein the lactide production process is a continuous process.

9. Method according to claim 8, wherein the amount of impurities in the lactide is quantified simultaneously at different stages of the continuous lactide production process.

10. Method according to claim 9, wherein the quantification of the amounts of the impurities is used to control production parameters, in order to adjust the continuous lactide production process.

* * * * *